US008603502B2

(12) United States Patent
Boulle et al.

(10) Patent No.: US 8,603,502 B2
(45) Date of Patent: Dec. 10, 2013

(54) COMPOSITIONS COMPRISING JASMONIC ACID DERIVATIVES AND USE OF THESE DERIVATIVES

(75) Inventors: Christophe Boulle, Langy S/Marne (FR); Maria Dalko, Gif S/Yvette (FR); Jean-Luc Leveque, Paris (FR); Lucie Simonetti, Vincennes (FR)

(73) Assignee: L'Oreal S.A., Paris (FR)

( * ) Notice: Subject to any disclaimer, the term of this patent is extended or adjusted under 35 U.S.C. 154(b) by 505 days.

(21) Appl. No.: 10/356,551

(22) Filed: Feb. 3, 2003

(65) Prior Publication Data

US 2004/0029839 A1 Feb. 12, 2004

Related U.S. Application Data

(60) Provisional application No. 60/357,620, filed on Feb. 20, 2002.

(30) Foreign Application Priority Data

Feb. 4, 2002 (FR) ...................................... 02 01279

(51) Int. Cl.
*A61K 31/557* (2006.01)

(52) U.S. Cl.
USPC ............................ 424/401; 514/530; 514/573

(58) Field of Classification Search
USPC ............................ 514/530, 573; 424/400, 901
See application file for complete search history.

(56) References Cited

U.S. PATENT DOCUMENTS

| 4,466,806 | A | | 8/1984 | Bugaut et al. |
| 4,603,146 | A | | 7/1986 | Kligman |
| 4,767,750 | A | | 8/1988 | Jacquet et al. |
| 4,906,457 | A | * | 3/1990 | Ryan ................................ 424/59 |
| 5,041,283 | A | | 8/1991 | Kita et al. |
| 5,300,489 | A | * | 4/1994 | Boden et al. ....................... 512/8 |
| 5,436,226 | A | * | 7/1995 | Lulai et al. ..................... 504/291 |
| 5,652,266 | A | | 7/1997 | Bobier-Rival et al. |
| 5,720,944 | A | | 2/1998 | Kiyomine et al. |
| 6,333,180 | B1 | | 12/2001 | Farbood et al. |
| 6,410,595 | B1 | * | 6/2002 | Neal ............................... 514/573 |
| 6,465,421 | B1 | | 10/2002 | Duranton et al. |
| 6,469,061 | B1 | * | 10/2002 | Flescher et al. ................ 514/530 |
| 6,703,006 | B2 | | 3/2004 | Causton et al. |
| 7,098,189 | B2 | | 8/2006 | Malik |
| 2002/0086041 | A1 | | 7/2002 | Maignan et al. |

FOREIGN PATENT DOCUMENTS

| EP | 0 413 528 | 2/1991 |
| EP | 0 648 488 | 4/1995 |
| EP | 0 989 111 | 3/2000 |
| FR | 2718022 | 4/1994 |
| JP | 58-180410 | 10/1983 |
| JP | A H3-188194 | 8/1991 |
| JP | A H4-108761 | 4/1992 |
| JP | A H7 308197 | 11/1995 |
| JP | A H10-29935 | 2/1998 |
| JP | T H11-511474 | 10/1999 |
| JP | 2001-199832 | 7/2001 |
| JP | 2001-207188 | 7/2001 |
| WO | WO 93/10756 | 6/1993 |
| WO | WO 96/00206 | 1/1996 |

OTHER PUBLICATIONS

WO 96/00206 published Jan 4, 1996 (English abstract only).*
Ansel's Pharmaceutical Dosage forms and Drug Delivery Systems, 2005, Lippincott Williams and Wilkins, (8th ed.), pp. 276-278.*
Hiromasa Kiyota et al., "Lipase-catalyzed preparation of both enantiomers of methyl jasomonate," Tetrahedron: Asymmetry, vol. 12, No. 7, 2001, pp. 1035-1038.
Database CA, Chemical Abstracts Service, Columbus, Ohio, US, Database Accession No. 131:28910, XP002214852, 1999.
Database CA, Chemical Abstracts Service, Columbus, Ohio, US, Database Accession No. 130-352121, XP002214853, 1999.
Database CA, Chemical Abstracts Service, Columbus, Ohio, US, Database Accession No. 130:279324, XP002214854, 1999.
Database CA, Chemical Abstracts Service, Columbus, Ohio, US, Database Accession No. 118:118844, XP002214855, 1999.
Co-pending Application No. Title: Compositions Comprising Cyclopentant Derivatices and Their Use Inventor(s): Jean-Luc Leveoue et al. U.S. Filing Date; Feb. 3, 2003.
English language abstract of JP 2001-207188, Jul. 31, 2000.
English language abstract of JP 58-180410, Oct. 21, 1983.
English language abstract of JP-A H7 308197, Nov. 28, 1995.
English language abstract of JP-A H10-29935, Mar. 3, 1998.
English language abstract of JP-A H3-188194 , Aug. 16, 1991.

(Continued)

*Primary Examiner* — Gina C Justice
(74) *Attorney, Agent, or Firm* — Finnegan, Henderson, Farabow, Garrett & Dunner, LLP

(57) ABSTRACT

Cosmetic or pharmaceutical compositions comprising compounds of formula (I) and the corresponding salts thereof:

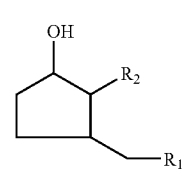

(I)

wherein:
$R_1$ is a radical chosen from —COOR', —CONR'R", —CH$_2$OR', —COR', —CH$_2$R', —SO$_2$OR', —PO$_3$R'R" and —NHR', wherein R' and R", which may be identical or different, are defined herein;
$R_2$ is chosen from saturated and unsaturated, linear, branched and cyclic hydrocarbon radicals comprising from 1 to 18 carbon atoms which are optionally substituted by from 1 to 5 identical or different entities chosen from —OR''', —OCOR''', —SR''', —SCOR''', NR'''R'''', —NHCOR''', halogen, —CN, —COOR''' and —COR''', wherein R''' and R'''', which may be identical or different, are defined herein, as well as the use of these compounds, for example, to promote skin desquamation, to stimulate epidermal renewal and/or to combat the signs of skin ageing.

33 Claims, No Drawings

(56) References Cited

OTHER PUBLICATIONS

English language abstract of JP-T-H11-511474, Oct. 5, 1999.
English language abstract of JP-A H4-108761, Apr. 9, 1992.
Herrmann, G., et al., "Biological Activity of Jasmonic Acid Conjugates," Comjugated Plant Horm. Proc. Int. Symp., Meeting Date 1986, pp. 315-322 (1997).
Ishikawa, A. et al., "Structure-Activity Relationships of Jasmonates in the Induction of Expression of Two Proteinase Inhibitor Genes of Potato," Bioscience, Biotechnology, and Biochemistry, vol. 58(3), pp. 544-547, (1994).
Office Action mailed Dec. 27, 2005, in co-pending U.S. Appl. No. 10/356,628.
Ward, K. et al., "The Induction of Proteinase Inhibitor II by Jasmonates," Proceedings of the Plant Growth Regulator Society of America, 23rd Edition, pp. 291-294, (1996).

\* cited by examiner

COMPOSITIONS COMPRISING JASMONIC ACID DERIVATIVES AND USE OF THESE DERIVATIVES

This application claims benefit of U.S. Provisional Application No. 60/357,620, filed Feb. 20, 2002.

This disclosure relates to cosmetic or pharmaceutical compositions comprising at least one jasmonic acid derivative. This disclosure also relates to the use of a composition comprising at least one jasmonic acid derivative, for example, to promote desquamation of the skin, to stimulate epidermal renewal and/or to combat ageing of the skin. This disclosure also relates to compositions, such as cosmetic or pharmaceutical compositions, which may be employed to promote desquamation of the skin and/or to stimulate epidermal renewal and therefore to combat intrinsic and/or extrinsic cutaneous ageing.

Desquamation is a natural phenomenon associated with the fact that the epidermis, which constitutes the upper layer of the skin, is continually being regenerated. The epidermis is composed of several layers of cells, the deepest of which is the basal layer, which is composed of undifferentiated cells. Over time, these cells differentiate and migrate towards the surface of the epidermis, making up the various layers thereof, until at the surface of the epidermis they form the corneocytes, which are dead cells that may be removed by desquamation. This loss at the surface is compensated by the migration of cells from the basal layer towards the surface of the epidermis. Thus, this phenomenon results in the perpetual renewal of the skin. Forced removal of the horny layer can accelerate the renewal and can make it possible to combat ageing.

While the cells migrate towards the surface of the epidermis, they continue their differentiation, until they reach the final stage, known as the corneocyte. These are in fact dead cells which make up the final layer of the epidermis, i.e., the outermost layer, also known as the stratum corneum.

Cutaneous ageing resulting from intrinsic or extrinsic factors can be manifested in the appearance of wrinkles and fine lines, in yellowing of the skin (which develops a parchment-like aspect accompanied by the appearance of pigmentary blemishes), in the disorganization of the elastin and collagen fibres (leading to a loss of elasticity, flexibility and firmness), or by the appearance of telangiectases.

Some of these signs of ageing are more particularly associated with intrinsic or physiological ageing, i.e. "normal" ageing, related to age, or chronobiological ageing. Others are more specific to extrinsic ageing, i.e. ageing brought about in general by the environment; for example, photo-ageing due to exposure to the sun, light, or any other radiation.

This disclosure concerns intrinsic or physiological ageing, as well as extrinsic ageing.

The changes in the skin owing to intrinsic ageing may be the consequence of a genetically programmed senescence involving endogenous factors. This intrinsic ageing may result, for example, in a slowdown in the renewal of the cells of the skin, which may be reflected by the appearance of detrimental clinical changes or histopathological changes. The clinical changes may include, for example, a reduction in the subcutaneous adipose tissue and the appearance of small wrinkles or fine lines. The histopathological changes may include, for example, an increase in the number and thickness of elastic fibres, a loss of vertical fibres from the membrane of the elastic tissue, and the presence of large irregular fibroblasts in the cells of this elastic tissue.

Extrinsic ageing may also lead to both detrimental clinical and histopathological changes. The clinical changes may include, for example, large wrinkles and the formation of a flaccid and weathered skin. The histopathological changes may include, for example, an excessive accumulation of elastic material in the upper dermis and degeneration of the collagen fibres.

Various agents intended to combat cutaneous ageing are known in the prior art.

U.S. Pat. No. 4,603,146 discloses the use of retinoic acid and its derivatives in cosmetic compositions, for the purpose of combating cutaneous ageing.

Moreover, many patents and publications (such as document EP-A-413 528) as well as many commercial cosmetic compositions teach the use of α-hydroxy acids, such as lactic acid, glycolic acid or citric acid, for treating cutaneous ageing.

In addition, β-hydroxy acids, such as salicylic acid and its derivatives, are known for their desquamating properties (see document WO-A 93/10756 and U.S. Pat. No. 4,767,750).

All these compounds have an action against ageing of the skin by promoting desquamation—i.e., the removal of the dead cells located at the surface of the horny layer of the epidermis. This desquamating property may also be referred to as a keratolytic property.

However, the compounds of the prior art can also have side effects, for example, stinging, stabbing pains, sensations of heat, and the appearance of red blotches which can be unpleasant for the user.

Thus, there is a need for anti-ageing agents that can minimize or avoid at least one of the disadvantages of the prior art.

The inventors have surprisingly found that it is possible to promote desquamation of the skin and/or stimulate epidermal renewal, while possibly minimizing or avoiding at least one of the disadvantages, for example, stinging, stabbing pains, sensations of heat and red blotches which may be unpleasant for the user.

Accordingly, disclosed herein, is a cosmetic or pharmaceutical composition comprising, in a physiologically acceptable medium, at least one entity chosen from compounds of formula (I), as defined below in paragraph [023], and the corresponding salts thereof. As is evident from the structure of formula (I) set forth below in paragraph [023], each compound of formula (I) contains at least three assymetric carbons, which can also be referred to as chiral centers, and thus each compound of formula (I) can represent at least eight stereoisomers. As defined herein, the at least one entity can be chosen from any combination of the stereoisomers of formula (I), i.e., one stereoisomer, all stereoisomers, and more than one stereoisomer but less than all stereoisomers.

Also disclosed herein is the use of the at least one entity to prepare a pharmaceutical composition for caring for the skin, for example, to promote desquamation of the skin, to stimulate epidermal renewal, to combat the signs of skin ageing, to enhance the complexion and/or to smoothen the skin of the face.

Further disclosed herein is the cosmetic use of the at least one entity or a cosmetic composition comprising it, wherein the at least one entity or cosmetic composition may be used for caring for the skin, for example, to promote desquamation of the skin, to stimulate epidermal renewal, to combat the signs of skin ageing, to enhance the complexion and/or to smoothen the skin of the face.

Even further disclosed herein is a method of cosmetic treatment to promote desquamation of the skin, to stimulate epidermal renewal, to combat the signs of skin ageing, to enhance the complexion and/or to smoothen the skin of the face, comprising applying to skin a cosmetic composition as defined below.

It has been observed that the at least one entity disclosed herein may present good solubility in water, which may facilitate the utilization.

The at least one entity as disclosed herein and described above in paragraph [018] is chosen from compounds of the following formula (I) and the corresponding salts thereof:

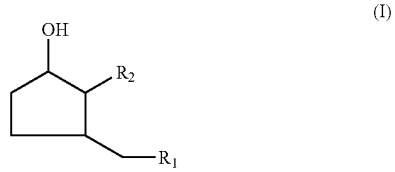

wherein:

- $R_1$ is a radical chosen from —COOR', —CONR'R", —CH$_2$OR', —COR', —CH$_2$R', —SO$_2$OR', —PO$_3$R'R" and —NHR', wherein R' and R", which may be identical or different, are chosen from a hydrogen atom and saturated and unsaturated, linear, branched and cyclic hydrocarbon radicals comprising from 1 to 18 carbon atoms, which may be optionally substituted by from 1 to 5 identical or different entities chosen from —OR''', —OCOR''', —SR''', —SCOR''', NR'''R'''', —NHCOR''', halogen, —CN, —COOR''' and —COR''', wherein R''' and R'''', which may be identical or different, are chosen from a hydrogen atom, aryl radicals and saturated and unsaturated, linear and branched hydrocarbon radicals comprising from 1 to 4 carbon atoms;
- $R_2$ is chosen from saturated and unsaturated, linear, branched and cyclic hydrocarbon radicals, comprising from 1 to 18 carbon atoms which may be optionally substituted by from 1 to 5 identical or different entities chosen from —OR''', —OCOR''', —SR''', —SCOR''', NR'''R'''', —NHCOR''', halogen, —CN, —COOR''' and —COR''', wherein R''' and R'''', which may be identical or different, are chosen from a hydrogen atom, aryl radicals and saturated and unsaturated, linear and branched hydrocarbon radicals comprising from 1 to 4 carbon atoms.

In one embodiment, the radical $R_1$ is chosen from —COOR', —CONR'R" and —CH$_2$OR', wherein R' and R", which may be identical or different, are chosen from a hydrogen atom and saturated and unsaturated, linear, branched and cyclic hydrocarbon radicals comprising from 1 to 18 carbon atoms, for example, from 1 to 12 carbon atoms, and further, for example, from 1 to 8 carbon atoms.

In another embodiment, the radical $R_1$ is chosen from the radicals —COOH, —CH$_2$OH, —COOCH$_3$, —COOC$_2$H$_5$, —COOC$_3$H$_7$—CONHCH$_3$ and —CONHC$_2$H$_5$.

In one embodiment, the radical $R_2$ is chosen from saturated and unsaturated, linear, branched, and cyclic hydrocarbon radicals comprising from 1 to 18 carbon atoms, for example, from 1 to 12 carbon atoms, and further for example, from 1 to 8 carbon atoms.

In another embodiment, the radical $R_2$ is chosen from saturated and linear hydrocarbon radicals comprising from 2 to 6 carbon atoms and linear hydrocarbon radicals comprising a single double unsaturation and comprising from 2 to 6 carbon atoms, and, for example, a radical —CH$_2$—CH=CH—C$_2$H$_5$ and, further for example, a radical —(CH$_2$)$_4$—CH$_3$.

In one embodiment, the salts of the compounds of formula (I) which may be used in accordance with this disclosure are chosen, for example, from the alkali metal and alkaline earth metal salts, the zinc, magnesium and strontium salts, salts with an organic amine, and the quaternary ammonium salts.

In another embodiment, the salts of the compounds of formula (I) according to this disclosure are chosen, for example, from the salts of an acid chosen from organic and inorganic acids, such as hydrochlorides, hydrobromides, and citrates.

In one embodiment, the at least one entity which may be used in the context of this disclosure may be chosen from:
3-hydroxy-2-[(2Z)-2-pentenyl]cyclopentaneacetic acid,
methyl 3-hydroxy-2-[(2Z)-2-pentenyl]cyclopentaneacetate,
2-[(2Z)-2-pentenyl]-3-hydroxycyclopentaneethanol,
3-hydroxy-2-pentylcyclopentaneacetic acid,
methyl 3-hydroxy-2-pentylcyclopentaneacetate, and
2-pentyl-3-hydroxycyclopentaneethanol.

The amount of the at least one entity chosen from compounds of formula (I) and the corresponding salts thereof, which may be used in accordance with this disclosure, depends on the desired effect and should be an amount effective for promoting desquamation of the skin and/or stimulating epidermal renewal and therefore combating intrinsic and/or extrinsic skin ageing.

In one embodiment, the amount of the at least one entity chosen from compounds of formula (I) and the corresponding salts thereof, which may be used in accordance with this disclosure, may range, for example, from 0.01 to 20%, further, for example, from 0.5 to 10%, and even further, for example, from 1 to 5% by weight, relative to the total weight of the composition.

The composition comprising the at least one entity chosen from compounds of formula (I) and the corresponding salts thereof may further comprise a physiologically acceptable medium, i.e., a medium which is compatible with a keratin material such as skin, scalp, nails, mucosae, eyes and hair or any other cutaneous region of a body. This composition may be a cosmetic or pharmaceutical composition and may therefore comprise a cosmetically or pharmaceutically acceptable medium.

The physiologically acceptable medium may comprise water and at least one organic solvent chosen, for example, from $C_1$-$C_8$ alcohols, for example, ethanol, isopropanol, tert-butanol and n-butanol; polyols such as glycerol; glycols such as butylene glycol, isoprene glycol, propylene glycol, and polyethylene glycols such as PEG-8; and polyol ethers.

The composition may also comprise at least one fatty phase, which may comprise at least one of oils, gums and waxes, which are commonly used in the field of application in question. These oils, gums, and waxes may be chosen, for example, from mineral oils (liquid petrolatum), vegetable oils (liquid fraction of karite butter, sunflower oil), animal oils (perhydrosqualene), synthetic oils (purcellin oil), silicone oils and waxes (cyclomethicone) and fluorinated oils (perfluoropolyethers), beeswax, carnauba wax and paraffin wax. Fatty alcohols and fatty acids (stearic acid) may be added to these oils.

When the composition is an emulsion, the proportion of the at least one fatty phase may range, for example, from 5% to 80% by weight and further, for example, from 5% to 50% by weight with respect to the total weight of the composition. The oils, waxes, emulsifiers and coemulsifiers used in the composition in the form of an emulsion may be chosen from those conventionally used in the cosmetics field. The emulsifier and the coemulsifier may be present in the composition in a proportion ranging, for example, from 0.3% to 30% by weight and further, for example, from 0.5 to 20% by weight with respect to the total weight of the composition. In addition, the emulsion may comprise at least one lipid vesicle.

When the composition is a solution or oily gel, the at least one fatty phase may represent, for example, more than 90% by weight of the total weight of the composition.

The composition may also comprise at least one adjuvant commonly used in the field under consideration, chosen, for example, from surfactants, emulsifiers, hydrophilic and lipophilic gelling agents, hydrophilic and lipophilic additives, preservatives, antioxidants, solvents, fragrances, fillers, screening agents, odour absorbers and colourants. The amount of the at least one adjuvant may be that conventionally used in the cosmetics field and may range, for example, from 0.01% to 10% by weight of the total weight of the composition. These adjuvants, depending on their nature, may be introduced into the fatty phase, into the aqueous phase and/or into the lipid spherules.

The surfactants, which can be used, include, for example, glycerol stearate, polysorbate 60 and the PEG-6/PEG-32/Glycol Stearate mixture sold under the name of Tefose® 63 by Gattefosse.

The hydrophilic gelling agents, which can be used, include, for example, carboxyvinyl polymers (carbomer), acrylic copolymers, such as acrylate/alkyl acrylate copolymers, polyacrylamides, polysaccharides, such as hydroxypropylcellulose, natural gums and clays. The lipophilic gelling agents include, for example, modified clays, such as bentones, metal salts of fatty acids, such as aluminium stearates, and hydrophobic silica, ethylcellulose and polyethylene.

The hydrophilic active agents include, for example, proteins and protein hydrolysates, amino acids, polyols, urea, allantoin, sugars and sugar derivatives, water-soluble vitamins, plant extracts and hydroxy acids.

The lipophilic active agents, including, for example, retinol (vitamin A) and its derivatives, tocopherol (vitamin E) and its derivatives, essential fatty acids, ceramides, essential oils, and salicylic acid and its derivatives may be used.

As disclosed herein, the composition may comprise at least one entity as defined above and at least one other active agent, chosen, for example, from:

- agents which may improve hair re-growth and/or act to slow down hair loss, for example, nicotinic esters, for example, tocopherol nicotinate; benzyl nicotinate and $C_1$-$C_6$ alkyl nicotinates, such as methyl and hexyl nicotinates, pyrimidine derivatives, such as 2,4-diamino-6-piperidinopyrimidine 3-oxide or "Minoxidil"; and agents which can promote hair re-growth, such as those disclosed by European patent application No. 0 648 488;
- agents which can vary cutaneous pigmentation and/or proliferation and/or differentiation, such as retinoic acid and its isomers, retinol and its esters, vitamin D and its derivatives, oestrogens, such as oestradiol, kojic acid, and hydroquinone;
- antibacterials, such as clindamycin phosphate, erythromycin and antibiotics from the tetracycline class;
- agents for combating parasites, for example, metronidazole, crotamiton and pyrethroids;
- antifungals, for example, compounds belonging to the imidazole class, such as econazole, ketoconazole and miconazole and their salts, polyene compounds, such as amphotericin B, compounds of the allylamine family, such as terbinafine, and alternatively octopirox;
- antiviral agents, such as acyclovir;
- steroidal anti-inflammatory agents, such as hydrocortisone, betamethasone valerate and clobetasol propionate, and non-steroidal anti-inflammatory agents, such as, ibuprofen and its salts, diclofenac and its salts, acetylsalicylic acid, acetaminophen and glycyrrhizic acid;
- anaesthetic agents, such as lidocaine hydrochloride and its derivatives;
- antipruritic agents, such as thenaldine, trimeprazine and cyproheptadine;
- keratolytic agents, such as α- and β-hydroxycarboxylic acids and β-ketocarboxylic acids, their salts, amides and esters and, for example, hydroxy acids, such as glycolic acid, lactic acid, salicylic acid, citric acid and generally fruit acids, and 5-(n-octanoyl)salicylic acid;
- free-radical scavengers, such as α-tocopherol and its esters, superoxide dismutases, certain metal chelating agents and ascorbic acid and its esters;
- antiseborrhoeics, such as progesterone;
- antidandruff agents, such as octopirox and zinc pyrithione;
- antiacne agents, such as retinoic acid and benzoyl peroxide; and
- extracts of plant, marine and bacterial origin.

The composition may be provided in any envisageable pharmaceutical form.

In one embodiment, the composition may be in a form chosen from aqueous, alcoholic, aqueous-alcoholic and oily solutions; dispersions of the lotion and serum type; water-in-oil, oil-in-water and multiple emulsions; suspensions; microcapsules and microparticles; vesicular dispersions of ionic and non-ionic type; aqueous, oily and serum-form lotions; capsules, granules, syrups, tablets; foams, solid preparations; and aerosol compositions further comprising at least one pressurized propellant.

In another embodiment, the composition as disclosed herein may be provided in a form of a haircare composition chosen from, for example, a shampoo, a hairsetting lotion, a treatment lotion, a styling cream and a styling gel, a dyeing composition, for example, an oxidation dyeing composition, hair restructuring lotions, a perming composition (for example, a composition for the first step of a permanent waving treatment), a lotion and a gel for combating hair loss and an antiparasitic shampoo.

In yet another embodiment, the composition may also be provided in a form of a composition chosen from cleansing, protective, treatment and care compositions for face, hands, feet, major anatomical folds and body, for example, day creams, night creams, makeup remover creams, sunscreen compositions, protective and care body milks, after-sun milks, skincare lotions, gels and mousses, such as cleansing lotions, artificial tanning compositions; facial and body makeup compositions such as foundations; bath compositions; deodorizing compositions comprising, for example, at least one bactericide; after-shave compositions; hair remover compositions; compositions to counter insect bites; pain relief compositions; and compositions for treating certain diseases of the skin, such as eczema, rosacea, psoriasis, lichens and severe pruritus.

The composition as disclosed herein may be applied as a cosmetic or pharmaceutical composition intended for the care of the skin of a face, body or scalp, such as to promote skin desquamation, stimulate epidermal renewal, combat the signs of skin ageing, enhance the complexion and/or smoothen the skin of the face.

Embodiments described herein are illustrated in more detail in the following non-limiting examples.

EXAMPLE 1

Synthesis of (+/−)(1R,2R)-3-hydroxy-2-[(2Z)-2-pentenyl]cyclopentaneacetic acid of formula

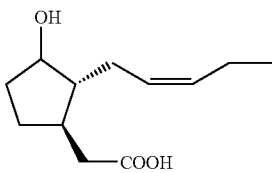

Operation 1: Synthesis of (+/−)-jasmonic acid or (+/−)(1R,2R)-3-oxo-2-[(2Z)-2-pentyl]cyclopentaneacetic acid

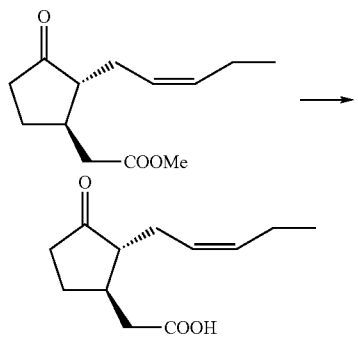

In a 250 ml three-necked flask equipped with a condenser, a thermometer and a magnetic stirrer, 15 g (66.9 mmol) of methyl (+/−)-jasmonate were dissolved in 150 ml of acetone. 10 ml of aqueous sodium hydroxide solution (5.35 g, 133.7 mmol) were added slowly. The mixture was stirred at room temperature for 5 hours. The acetone was then evaporated under vacuum and the residual aqueous phase was subsequently washed with ethyl acetate (2×30 ml). The aqueous phase was acidified to pH=2 using hydrochloric acid and was then extracted with dichloromethane (3×30 ml).

The organic phase was dried over sodium sulphate, filtered on filter paper and then concentrated. The light brown oil obtained was dried under vacuum.

This gave 13.6 g of (+/−)-jasmonic acid, i.e. a yield of 97%.

The $^1$H NMR spectrum and the mass spectrum (negative ionization) are in accordance with the expected structure.

Operation 2: Synthesis of (+/−)(1R,2R)-3-hydroxy-2-[(2Z)-2-pentenyl]cyclopentaneacetic acid

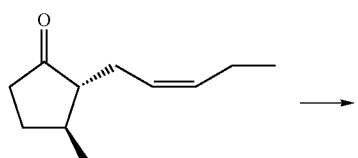

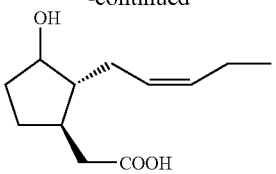

In a 50 ml three-necked flask equipped with a condenser, a thermometer and a magnetic stirrer, 1 g (4.8 mmol) of (+/−)-jasmonic acid was dissolved in 15 ml of absolute ethanol. 430 mg (11.4 mmol) of sodium borohydride, NaBH$_4$, were added. The mixture was stirred at 50° C. for 4 hours. When the reaction was finished, 5 ml of water were added slowly. The precipitate formed was filtered off. The filtrate was acidified to pH=5 with hydrochloric acid and then extracted with ethyl acetate (3×30 ml). The organic phase was dried over sodium sulphate, filtered on filter paper, and then concentrated. The colourless oil obtained was purified by chromatography on silica gel (eluent: dichloromethane/methanol). The colourless oil obtained was dried under vacuum.

This gave 400 mg of the target compound, i.e. a yield of 40%.

The $^1$H NMR spectrum is in accordance with the expected structure.

EXAMPLE 2

Synthesis of (+/−)(1R,2R)-2-[(2Z)-2-pentenyl]-3-hydroxycyclopentaneethanol of Formula

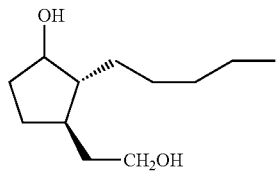

Reaction scheme

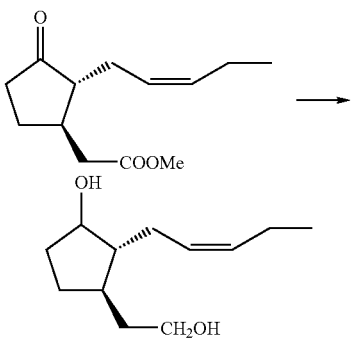

In a 50 ml three-necked flask equipped with a condenser, a thermometer and a magnetic stirrer, 1 g (4.5 mmol) of methyl (+/−)-jasmonate was dissolved in 15 ml of tetrahydrofuran. 430 mg (11.3 mmol) of lithium aluminium hydride, LiAlH$_4$, were added. The mixture was stirred at 50° C. for 4 hours. When the reaction was finished, 5 ml of water were added slowly. The precipitate formed was filtered off and the filtrate was acidified to pH=5 with hydrochloric acid and then extracted with ethyl acetate (3×30 ml). The organic phase was dried over sodium sulphate, filtered on filter paper, and then concentrated. The colourless oil obtained was purified by chromatography on silica gel (eluent: dichloromethane/methanol). The colourless oil obtained was dried under vacuum.

This gave 550 mg of the target compound, i.e. a yield of 62%.

The $^1$H NMR spectrum is in accordance with the expected structure.

EXAMPLE 3

Synthesis of (+/−)(1R,2R)-3-hydroxy-2-pentylcyclopentaneacetic acid of formula

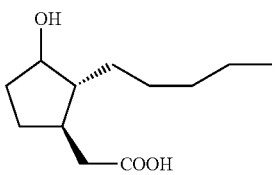

Operation 1: Synthesis of (+/−)-dihydrojasmonic acid or (+/−)(1R,2R)-3-oxo-2-pentylcyclopentaneacetic acid of formula

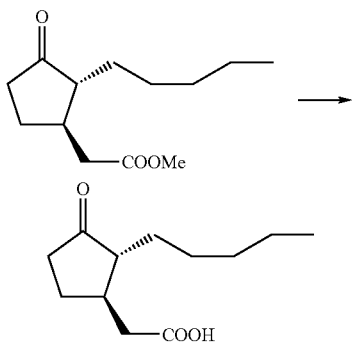

In a 250 ml three-necked flask equipped with a condenser, a thermometer and a magnetic stirrer, 5 g (23.6 mmol) of methyl (+/−)-dihydrojasmonate were dissolved in 50 ml of acetone. 10 ml of aqueous sodium hydroxide solution (1.76 g, 44 mmol) were added slowly. The mixture was stirred at room temperature for 5 hours. The acetone was then distilled off under vacuum, and the residual aqueous phase was then washed with ethyl acetate (2×20 ml). The aqueous phase was acidified to pH=2 with hydrochloric acid. This phase was then extracted with dichloromethane (2×30 ml). The organic phase was dried over sodium sulphate, filtered on filter paper, and then concentrated. The oil obtained was purified by chromatography on silica gel (eluent: dichloromethane/methanol). The oil obtained was dried under vacuum.

This gave 1.7 g of the target compound, i.e. a yield of 36%.

The $^1$H NMR spectrum is in accordance with the expected structure.

Operation 2: Synthesis of (+/−)(1R,2R)-3-hydroxy-2-pentylcyclopentaneacetic acid

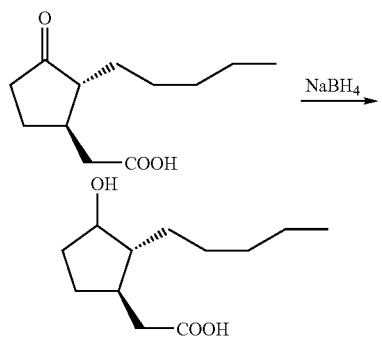

This compound was prepared in a way similar to that described in operation 2 of Example 1, by reacting dihydrojasmonic acid with sodium borohydride, NaBH$_4$, in ethanol at 50° C. for 4 hours.

The target compound was obtained with a yield of 45%.

The $^1$H NMR spectrum is in accordance with the expected structure.

EXAMPLE 4

Synthesis of (+/−)(1R,2R)-2-pentyl-3-hydroxycyclopentaneethanol of formula

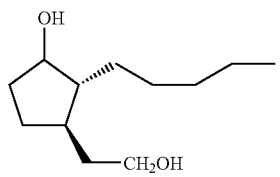

Reaction scheme

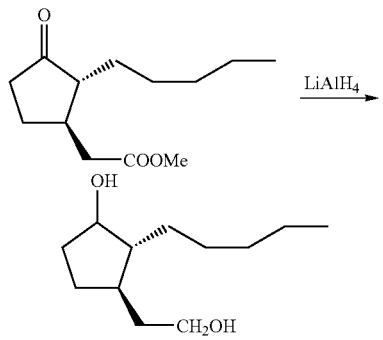

This compound was prepared in a way similar to that described in Example 2, by reacting methyl dihydrojasmonate in tetrahydrofuran with lithium aluminium hydride at 50° C. for 4 hours.

The target compound was obtained with a yield of 68%.
The $^1$H NMR spectrum is in accordance with the expected structure.

EXAMPLE 5

Activity Tests

The keratolytic power of a number of compounds of this disclosure was studied. This test comprises counting corneocytes released following incubation of patches of isolated stratum corneum in the presence of the test compounds.

Stratum corneum isolated by trypsin/heat from surgical plasties was used. A number of different stratum corneum samples were used. Discs of 4 mm in diameter were punched out and placed at the bottom of a 96-well plate.

Test 1

A 1% by weight solution of the compound of Example 3 was prepared in a PBS buffer supplemented with 0.1% of Triton X100. The pH of the solution was adjusted to 7.4.

50 microliters of test solution or of control solution (PBS buffer supplemented with 0.1% of Triton X100) were added to each well. Incubation was carried out at 37° C. with stirring for 24 hours.

10 microliters of solution were then withdrawn and were placed in a Malassez cell. The liberated corneocytes were counted under the microscope.

The results obtained are as follows, expressed as the number of liberated corneocytes per microliter, averaged over three tests. Corneocyte fragments were not counted.

|  | Sample 1* | Sample 2* | Sample 3* | Average |
|---|---|---|---|---|
| Example 3 | 28 ± 9 | 56 ± 7 | 101 ± 11 | 61 ± 33 |
| Control | 4 ± 4 | 8 ± 3 | 17 ± 8 | 9 ± 8 |

*average over three tests

The number of corneocytes liberated after incubation of the isolated stratum corneum with the compound of this disclosure is much greater than the number liberated in the presence of the buffer on its own.

Test 2

A 1% by weight solution of the compound of Example 1, or jasmonic acid (comparison), was prepared in a PBS buffer supplemented with 0.1% of Triton X100. The pH of the solution was adjusted to 7.4.

50 microliters of test solution or of control solution (PBS buffer supplemented with 0.1% of Triton X100) were added to each well. Incubation was carried out at 37° C. with stirring for 24 hours.

10 microliters of solution were then withdrawn and were placed in a Malassez cell. The liberated corneocytes were counted under the microscope.

The results obtained are as follows, expressed as the number of liberated corneocytes per microliter, averaged over three tests. Corneocyte fragments are not counted.

|  | Average (3 tests per sample, 3 different samples) |
|---|---|
| Example 1 | 26 ± 7 |
| Jasmonic acid | 15 ± 5 |
| Control | 9 ± 3 |

Test 3

A 2% by weight solution of the compound of Example 3, or 2-hydroxy-4-octanoylbenzoic acid (comparison), was prepared in an aqueous solution containing 50% by weight of polyethylene glycol (PEG 8) and 30% by weight of ethanol.

50 microliters of test solution or of control solution were added to each well. Incubation was carried out at 37° C. with stirring for 24 hours.

10 microliters of solution were then withdrawn and were placed in a Mallassez cell. The liberated corneocytes were counted under the microscope.

The results obtained are as follows, expressed as the number of liberated corneocytes per microliter, averaged over the three tests. Corneocyte fragments were not counted.

|  | Sample 1* | Sample 2* | Average |
|---|---|---|---|
| Example 3 | 2 ± 3 | 3 ± 1 | 2.5 ± 2 |
| 2-Hydroxy-4-octanoylbenzoic acid | 3 ± 3 | 4 ± 3 | 3.5 ± 3 |
| Control | 1 ± 1 | 1 ± 1 | 1 ± 1 |

*Average over three tests

EXAMPLE 6

An emulsion was prepared comprising (% by weight):

| | |
|---|---|
| compound of Example 1 | 1% |
| propylene glycol isostearate | 13% |
| polyethylene glycol (8 EO) | 5% |
| propylene glycol | 3% |
| pentylene glycol | 3% |
| glyceryl stearate and polyethylene glycol stearate (100 EO) | 5% |
| ethoxylated sorbitan monostearate (20 EO) | 0.5% |
| ethoxylated (20 EO) and propoxylated (5 PO) cetyl alcohol | 1% |
| gelling agent | 0.5% |
| $C_{12-15}$ alkyl benzoates | 4% |
| ethanol | 3% |
| sodium hydroxide | 0.12% |
| preservatives | qs |
| water | qs 100% |

What is claimed is:

1. A composition for skincare comprising
a) a cosmetically or pharmaceutically acceptable medium,
b) at least one entity chosen from compounds of formula (I) and the corresponding salts thereof:

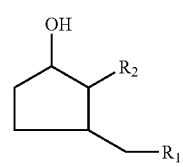

(I)

wherein:
  $R_1$ is a radical —COOH;
  $R_2$ is chosen from saturated linear, branched and cyclic hydrocarbon radicals comprising from 1 to 8 carbon atoms and
c) at least one adjuvant chosen from a silicone oil, fluorinated oil, a gum, a wax, a hydrophilic active agent, a lipophilic active agent, a preservative, an antioxidant, a fragrance, a filler, a screening agent, an odor absorber, and a colorant, wherein the composition is effective for skincare.

2. The composition according to claim 1, wherein the radical $R_2$ is chosen from saturated linear hydrocarbon radicals comprising from 2 to 6 carbon atoms.

3. The composition according to claim 2, wherein the radical $R_2$ is —$(CH_2)_4$—$CH_3$.

4. The composition according to claim 1, wherein the at least one entity is chosen from:
3-hydroxy-2-pentylcyclopentaneacetic acid.

5. The composition according to claim 1, wherein the at least one entity is present in an amount ranging from 0.01 to 20% by weight, relative to the total weight of the composition.

6. The composition according to claim 5, wherein the at least one entity is present in an amount ranging from 0.5 to 10% by weight, relative to the total weight of the composition.

7. The composition according to claim 6, wherein the at least one entity is present in an amount ranging from 1 to 5% by weight, relative to the total weight of the composition.

8. The composition according to claim 1, wherein the composition is provided in a form chosen from; cleansing, protective, treatment and care compositions for face, hands, feet, major anatomical folds and body; facial and body makeup compositions; bath compositions; deodorizing compositions; after-shave compositions; hair remover compositions; and compositions to counter insect bites.

9. The composition according to claim 8, wherein the cleansing, protective, treatment and care compositions for face, hands, feet, major anatomical folds and body are chosen from day creams, night creams, makeup remover creams, sunscreen compositions, protective and care body milks, after-sun milks, skincare lotions, gels and mousses, and artificial tanning compositions.

10. A pharmaceutical composition for skincare comprising
a) a pharmaceutically acceptable medium,
b) at least one entity chosen from compounds of formula (I) and the corresponding salts thereof:

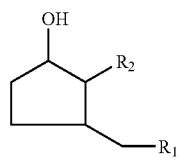

(I)

wherein:
R1 is a radical-COOH;
$R_2$ is chosen from saturated, linear, branched and cyclic hydrocarbon radicals comprising from 1 to 8 carbon atoms and
c) at least one adjuvant chosen from a silicone oil, fluorinated oil, a gum, a wax, a hydrophilic active agent, a lipophilic active agent, a preservative, an antioxidant, a fragrance, a filler, a screening agent, an odor absorber, and a colorant,
wherein the pharmaceutical composition is effective for skincare.

11. The pharmaceutical composition according to claim 10, wherein the pharmaceutical composition is effective to achieve at least one effect chosen from promoting skin desquamation, stimulating epidermal renewal, combating the signs of skin ageing, enhancing facial complexion and smoothening the skin of a face.

12. The composition according to claim 1, wherein the at least one entity is chosen from 3-hydroxy-2-pentylcyclopentane acetic acid of the Formula:

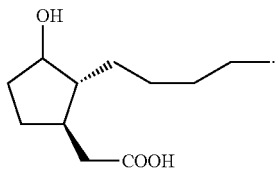

13. The composition according to claim 12, wherein the at least one entity is present in an amount ranging from 0.01 to 20% by weight, relative to the total weight of the composition.

14. The composition according to claim 13, wherein the at least one entity is present in an amount ranging from 0.5 to 10% by weight, relative to the total weight of the composition.

15. The composition according to claim 14, wherein the at least one entity is present in an amount ranging from 1 to 5% by weight, relative to the total weight of the composition.

16. A composition for skincare comprising,
a) a cosmetically acceptable medium,
b) at least one entity, present in an amount ranging from 0.01 to 20% by weight relative to the total weight of the composition, chosen from compounds of formula (I) and the corresponding salts thereof:

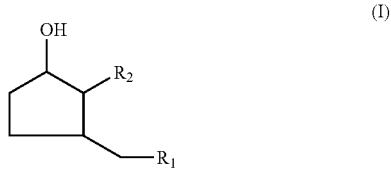

(I)

wherein:
$R_1$ is a radical —COOR', wherein R' is chosen from a hydrogen atom and saturated and unsaturated, linear, branched and cyclic hydrocarbon radicals comprising from 1 to 18 carbon atoms;
$R_2$ is chosen from saturated linear, branched and cyclic hydrocarbon radicals comprising from 1 to 8 carbon atoms and
c) at least one adjuvant chosen from a silicone oil, fluorinated oil, a gum, a wax, a hydrophilic active agent, a lipophilic active agent, a preservative, an antioxidant, a fragrance, a filler, a screening agent, an odor absorber, and a colorant,
wherein the composition is effective for skincare.

17. The composition according to claim 16, wherein the radical R1 is chosen from —COOR', wherein R' is chosen from a hydrogen atom and saturated and unsaturated, linear, branched and cyclic hydrocarbon radicals comprising from 1 to 12 carbon atoms.

18. The composition according to claim 17, wherein R' is chosen from a hydrogen atom and saturated and unsaturated, linear, branched and cyclic hydrocarbon radicals comprising from 1 to 8 carbon atoms.

19. The composition according to claim 16, wherein the radical R1 is chosen from the radicals —COOH, —$COOCH_3$, —$COOC_2H_5$, and —$COOC_3H_7$.

20. The composition according to claim 16, wherein R2 is chosen from saturated and linear hydrocarbon radicals comprising from 2 to 6 carbon atoms.

21. The composition according to claim 20, wherein $R_2$ is —$(CH_2)_4$—$CH_3$.

22. The composition according to claim 16, wherein the at least one entity is present in an amount ranging from 0.5 to 10% by weight, relative to the total weight of the composition.

23. The composition according to claim 22, wherein the at least one entity is present in an amount ranging from 1 to 5% by weight, relative to the total weight of the composition.

24. The pharmaceutical composition according to claim 10, wherein the at least one entity is 3-hydroxy-2-pentylcyclopentaneacetic acid.

25. The composition according to claim 16, wherein the at least one entity is chosen from 3-hydroxy-2-pentylcyclopentaneacetic acid.

26. The cosmetic composition according to claim 16, wherein the cosmetic composition is effective to achieve at least one effect chosen from promoting skin desquamation, stimulating epidermal renewal, combating the signs of skin ageing, enhancing facial complexion, and smoothening the skin of a face.

27. The composition of claim 1, wherein the compound of formula (I) is chosen from an alkali metal salt of the compound of formula (I).

28. The composition of claim 4 wherein the compound of formula (I) is chosen from an alkali metal salt of the compound of formula (I).

29. The pharmaceutical composition for skincare of claim 10, wherein the compound of formula (I) is chosen from an alkali metal salt of the compound of formula (I).

30. The composition for skincare according to claim 12, wherein the compound of formula (I) is chosen from an alkali metal salt of the compound of formula (I).

31. The composition for skincare according to claim 16, wherein the compound of formula (I) is chosen from an alkali metal salt of the compound of formula (I).

32. The pharmaceutical composition for skincare according to claim 24, wherein the compound of formula (I) is chosen from an alkali metal salt of the compound of formula (I).

33. The composition for skincare according to claim 25, wherein the compound of formula (I) is chosen from an alkali metal salt of the compound of formula (I).

* * * * *